(12) United States Patent
Büttner et al.

(10) Patent No.: US 6,258,238 B1
(45) Date of Patent: Jul. 10, 2001

(54) METHOD OF PRODUCING A CAPILLARY, A CAPILLARY FOR AN ELECTROPHORESIS DEVICE AND AN ELECTROPHORESIS DEVICE INCLUDING SUCH A CAPILLARY

(75) Inventors: Christian Büttner, Waldbronn (DE); Wolfgang D T. Beck, Visp (CH)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/650,529

(22) Filed: Aug. 30, 2000

Related U.S. Application Data

(63) Continuation of application No. 08/259,471, filed on Jun. 14, 1994, now abandoned.

(30) Foreign Application Priority Data

Jul. 12, 1993 (EP) .................................................. 93111150

(51) Int. Cl.[7] .......................... G01N 27/26; G01N 27/447
(52) U.S. Cl. .......................... 204/603; 204/451; 204/452; 204/601
(58) Field of Search .................................... 204/601, 602, 204/603, 604, 605, 451, 452, 453, 454, 455

(56) References Cited

U.S. PATENT DOCUMENTS

| 5,061,361 | * | 10/1991 | Gordon | 204/452 |
| 5,246,577 | * | 9/1993 | Fuchs et al. | 206/604 |
| 5,324,413 | * | 6/1994 | Gordon | 204/603 |
| 5,429,728 | * | 7/1995 | Gordon | 204/453 |
| 5,658,446 | * | 8/1997 | Yin et al. | 204/451 |
| 5,908,552 | * | 6/1999 | Dittmann et al. | 204/601 X |
| 5,926,271 | * | 7/1999 | Couderc et al. | 356/318 |

\* cited by examiner

Primary Examiner—Jill Warden
Assistant Examiner—John S. Starsiakm Jr.

(57) ABSTRACT

A method for producing a capillary comprises the steps of providing first a capillary having a uniform inner width throughout its length, introducing then an etchant into the capillary, and producing a temperature gradient over the length of the capillary in such a way that a temperature-controlled increased expansion of the inner width of the capillary will take place during the etching process in the heated region thereof. A capillary produced in this way is excellently suitable for use in an electrophoresis device.

10 Claims, 4 Drawing Sheets

METHOD OF PRODUCING A CAPILLARY, A CAPILLARY FOR AN ELECTROPHORESIS DEVICE AND AN ELECTROPHORESIS DEVICE INCLUDING SUCH A CAPILLARY

This is a continuation of application Ser. No. 08/259,471, filed Jun. 14, 1994 now abandoned.

FIELD OF THE INVENTION

The present invention deals quite generally with a method of producing a capillary, and in particular with a capillary of the type which is adapted to be used for an electrophoresis device.

BACKGROUND OF THE INVENTION

There are various techniques for rapidly and accurately identifying small quantities of inorganic and organic substances. When such substances, whose molecular structure is comparatively small, are to be detected, gas chromatographs and liquid chromatographs have been used for this detection for years. Although chromatography proved to be a successful attempt to determine metals and inorganic mixtures as well as small organic ions, this technique used for determining a constituent part in a sample is not suitable for determining large and complex molecules, such as amino acids, proteins and DNA.

Hence, another analysis technique, which is called electrophoresis, has been used with great success for some years. This technique comprises the step of applying an electric field across the length of a capillary that contains a mixture of an unknown sample and a non-reactive liquid, which is referred to as sample solution. The electric field causes the constituents of the unknown sample to migrate through the capillary due to the electrical attraction created by the electric field. Different components within the sample are attracted at different rates due to their varying molecular properties (molecular drag) and varying electrical charges. Hence, the substances become increasingly separated into distinct zones or groups as they progress along the capillary. Each band of constituent material that makes up the original, unseparated mixture of the unknown sample material passes through the capillary. At some point along the capillary, the band is examined and identified by a detector. One typical detector for electrophoresis separation measures the electrical conductivity of the bands in the capillary. An alternative detection scheme uses fluorescence, for example laser induced fluorescence. Although this technique is comparatively sensitive, it is costly and limited to specific mixtures that can be stimulated to fluoresce.

In other electrophoresis systems, an optical detection technique is used, which comprises the step of measuring the light absorption caused by the bands, which are separated from one another over the electrophoresis path. In conventional electrophoresis devices, the sensitivity of this type of optical detection is only very low due-to the short path that the light travels through the interior of the capillary. An increase in the inner diameter of the capillary is, however, disadvantageous, since otherwise turbulences or eddy currents might occur, whereby the separation of the constituent parts caused by electrophoresis would become null and void.

However, such known electrophoresis systems with capillaries having a uniform outer and inner diameter throughout their length entail also additional problems. The voltage applied to the capillary ends drops uniformly across the whole capillary, when the capillary is filled completely. The part of this voltage which will result in a separation of the substances of the sample is only the part that drops across the separation path between the sample input or rather the inlet of the capillary and the detector. The residual voltage drop between the detector and the outlet of the capillary does not contribute in any way to the separation and will only cause losses. It follows that, in connection with such systems, comparatively complicated and costly measures are normally taken so as to obtain the shortest possible length of the capillary between the detector and the outlet end of the capillary.

An additional problem of this technique resides in the fact that the advantage of a capillary inner width which is as small as possible, viz. low loss power in combination with high mass selectivity, can only be obtained at the price of a loss of detection sensitivity.

U.S. Pat. No. 5,061,361 disclosed for the first time an electrophoretic system in which high mass sensitivity and low loss power can be obtained without having to put up with a low detection sensitivity. In the electrophoresis system according to U.S. Pat. No. 5,061,361, the capillary has an enlarged inner width at least in the area of the detector device so that a longer, effective detection path of the light between the light source and the sensor of the detector device through the fluid containing the constituent part to be detected will be obtained without any necessity of enlarging the capillary inner width of the residual part of the capillary. U.S. Pat. No. 5,061,361 describes a method of producing a capillary of this type comprising the steps of closing a capillary, which initially has a constant outer width and a constant inner width, on one side thereof and applying a low pressure to the interior thereof, whereupon said capillary is locally heated and simultaneously rotated so that a local gas bubble, which has to be arranged in the area of the detector device, will be formed. This production method, which is based on the principle of glass-blowing, is comparatively complicated. Due to the enlargement of the outer width of the capillary in the area of the bubble, it is not possible to use such a modified capillary as a substitute for a standard capillary in commercially available capillary electrophoresis devices.

SUMMARY OF THE INVENTION

One object of the present invention is to provide a simplified method of producing a capillary whose inner width can be varied along its length.

An additional object of the present invention is to provide a capillary which is adapted to be used for electrophoresis devices and which, in spite of having a low loss power, permits a high detection sensitivity in combination with a good separation effect.

Another object of the present invention is to provide a capillary which is adapted to be inserted into existing electrophoretic devices as a substitute for standard capillaries having an invariable inner width so as to enhance the detection sensitivity of such existing electrophoresis devices.

Finally, it is an object of the present invention to provide an electrophoresis device having a high detection sensitivity in combination with a low loss power and a high mass selectivity.

In accordance with a first aspect of the invention, this object is achieved by a method of producing a capillary comprising a first capillary area having a first inner width and a second capillary area having a second inner width which is enlarged in comparison with said first inner diameter, said method including the following steps:

providing a capillary which has an essentially uniform inner width over its length, introducing into the interior of the capillary an etchant by means of which the material of the capillary can be etched, producing a temperature gradient over the capillary in such a way that the temperature of the second capillary area is higher than the temperature of the first capillary area, and carrying out the etching process until the second capillary region has the desired inner width.

In a preferred embodiment, the method step of carrying out the etching process comprises the measure of causing the etchant to flow through the capillary.

In a further preferred embodiment, the method step of producing the temperature gradient comprises the following steps:

introducing one of the two capillary areas of the capillary into a hose, introducing the other capillary area into a bath having a predetermined temperature, passing through said hose a medium whose temperature differs from that of the bath.

In a further preferred embodiment, the bath is an ice water bath, and the medium passing through the hose is steam.

In a further preferred embodiment, the etchant flowing through the capillary is supplied to the capillary with overpressure.

In a further preferred embodiment, the capillary consists of quartz glass and the etchant is hydrofluoric acid HF.

In accordance with a second aspect of the invention, this object is achieved by a capillary for use in an electrophoretic device, comprising:

a first capillary area having a first inner width and a second capillary area having a second inner width which is enlarged in comparison with said first inner diameter, said first inner width merging with said second inner width continuously and without any steps and said first and second capillary areas having a corresponding outer width at least in their transition region.

In a further preferred embodiment, the second capillary area having a second inner width, which is enlarged in comparison with said first inner width, extends from the transition region to said first capillary area up to the end of the capillary located on the outlet side.

In accordance with a third aspect of the invention, this object is achieved by an electrophoresis device for detecting at least one constituent part of a sample, comprising:

a capillary for use in an electrophoretic device, comprising:

a first capillary area having a first inner width and a second capillary area having a second inner width which is enlarged in comparison with said first inner diameter, said first inner width merging with said second inner width continuously and without any steps and said first and second capillary areas having a corresponding outer width at least in their transition region, an input reservoir from which the first capillary area of the capillary extends, an outlet reservoir up to and into which the second capillary area of the capillary extends, a generator for producing an electric field between a buffer solution in the input reservoir and a buffer solution in the outlet reservoir; and an detector device comprising a light source and a light sensor arranged at the second capillary area of the capillary so as to detect the at least one constituent part of the sample.

In preferred embodiments of the invention, the detector device can either be an absorbance detector device or a fluorescence detector device.

Figure 1:
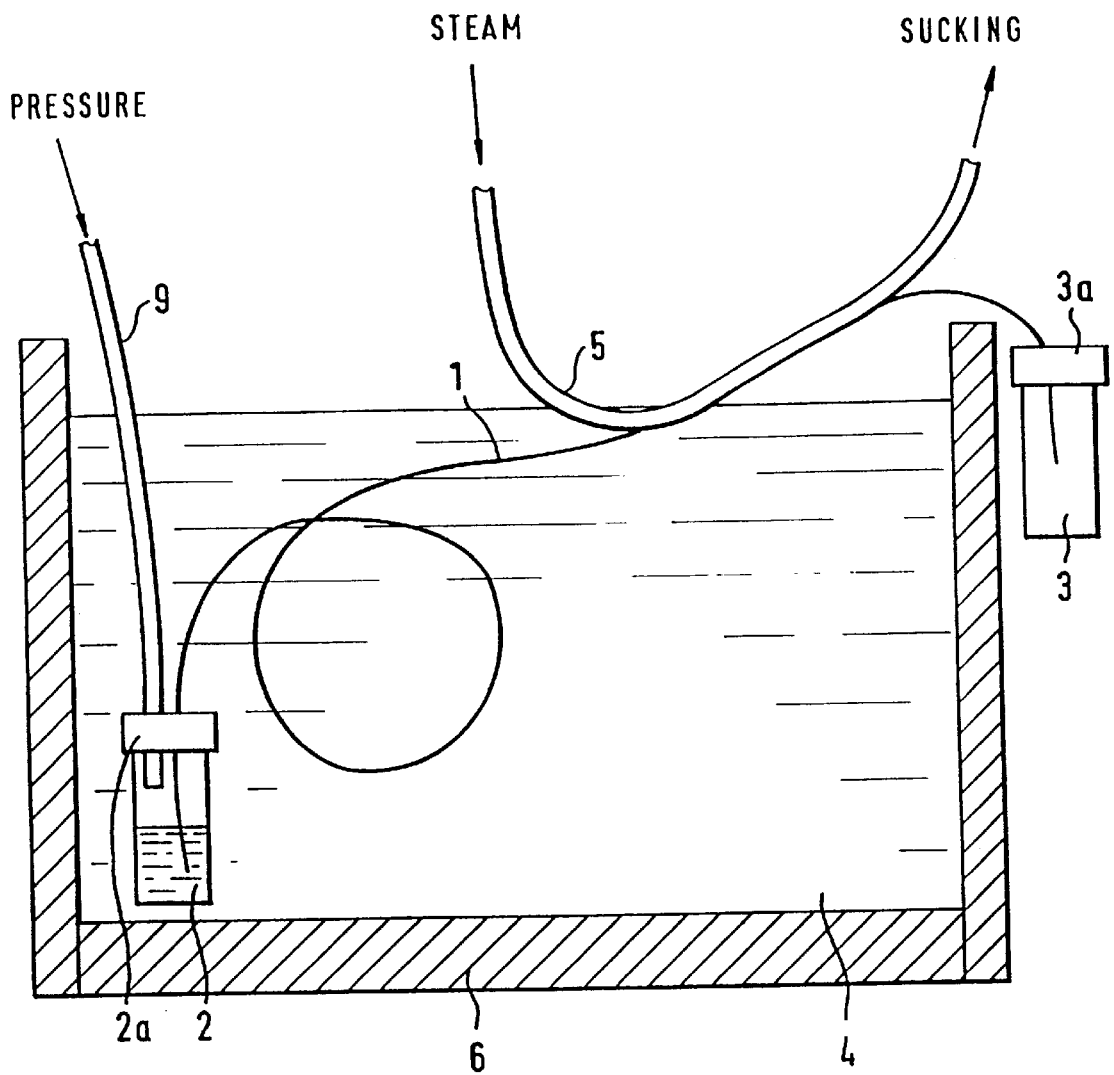
FIG. 1 shows a cross-sectional representation of a device for producing a capillary according to the present invention.

The device for carrying out the method according to the present invention, which is shown in FIG. 1, is used for etching off the inner area of a capillary 1, which consists a quartz capillary, in a controlled process. In the embodiment shown, the quartz capillary has a length of 80 cm, an outer width of 360 $\mu$m and an inner width of 50 $\mu$m. As can be seen from the finished capillary in FIG. 2, the production method aims at expanding, in the embodiment shown, the quartz capillary 1 from a first area, in which the capillary has an inner width of 50 $\mu$m, over a length of 150 mm up to the end of the capillary (not shown in FIG. 2) to an inner width of 150 $\mu$m.

The production device shown in FIG. I comprises an air-tight reservoir 2, which is filled with concentrated hydrofluoric acid HF and arranged in the interior of a receptacle 6 filled with an ice water bath 4, a collection vessel 3 arranged outside of said receptacle, a pressure supply hose 9 for applying an overpressure of approx. 4 bar to said reservoir 2, and a hose 5 through which steam can be supplied.

As will be explained in detail hereinbelow, the device shown in said figure permits, at the quartz capillary to be treated, the generation of a temperature gradient along a selectable longitudinal section at impressed temperatures of aprox. 100° Celsius and 0° Celsius.

For the purpose of heating a predetermined section of the capillary 1, a hose, which preferably consists of plastic material, is pierced at two spaced-apart locations, the distance between the holes being 15 cm, whereupon the capillary 1 is introduced into the hose 5 at one of these locations and emerges at the other. The ends of the capillary are guided—each through a septum 2a, 3a providing an air-tight closure—into the reservoir 2 and the collection vessel 3, respectively. The front of the capillary is introduced into the ice water bath 4 together with the reservoir 2 up to the point where the capillary enters the hose 5. Steam having a temperature of approx. 100° Celsius is now passed through the hose 5. Condensed water, which forms in the area of the capillaries, is removed by additional sucking off at the end of the hose.

The actual etching process for structuring the interior of the capillary begins with the application of an overpressure of approx. 4 bar to the pressure supply hose 9. After 15 minutes, the pressure which causes the etchant to flow through the interior of the capillary is switched off and, subsequently, the capillary is rinsed with water. After having been cut off to length, the capillary is ready for use.

Figure 2:
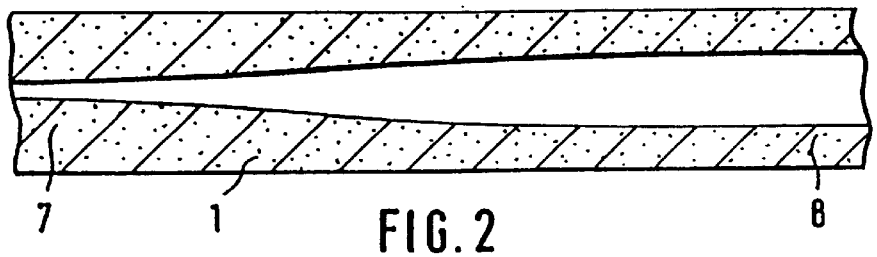
FIG. 2 shows a sectional view through a subsection of an embodiment of the capillary according to the present invention.

The expansion profile of the finished capillary, which, as has already been mentioned, is shown in FIG. 2 in a cross-sectional representation, shows a continuous transition from the inner width of 50 $\mu$m in a first area 7 of the capillary to an inner width of 150 $\mu$m in a second area 8 of the capillary, said second area 8 extending up to the end of the capillary 1. In addition to the geometries of the quartz capillary 1, it is essentially the boundary between the impressed temperatures that determines the transition region. In the present case, the boundary is the wall of the hose 5 at the point of passage with a thickness of approx. 1 mm. In the embodiment shown in FIG. 2, this results in a transition region between the first capillary area 7 and the second capillary area 8 over a capillary length of 1200 $\mu$m. Starting from an initially concentric position of the outer wall of the capillary and of the inner wall thereof, the inner boundary surfaces will expand concentrically during the etching process.

The etching rate and the width ratios between the inner width of the first capillary area 7 and the inner diameter of the second capillary area 8 can be controlled by the etching period and the temperature difference. This is based on the principle that, at higher temperatures, the etchant has a higher chemical activity. As a rule of thumb, each rise in temperature of 10° Celsius will approximately double the reaction rate.

Fundamentally, all means can be used for this method with the aid of which the inner walls of pierced quartz bodies are removed at different locations simultaneously or successively by adequate temperature gradients in a defined manner. It is not absolutely necessary to carry out the removal concentrically with the hole. The outer dimensions of the quartz body remain unchanged. Coated surfaces of the quartz, which may perhaps be provided, remain intact.

In the present embodiment, the capillary 1 is provided with an outer coating of polyamide. This polyamide coating remains intact. Also the external dimensions of the capillary 1 remain unchanged. This aspect is particularly important, as will be shown more clearly in the explanation following hereinbelow, in cases in which a capillary 1, which has been modified by the method according to the present invention, is to be used in a detector of a capillary-type electrophoretic device whose capillary support is designed for a capillary having a constant width.

The concentric removal which is obtained when the method according to the present invention is used and which provides a smooth, continuous transition between the first capillary area 7 having a small width and the second capillary area 8 having a large width is optimal with respect to the requirements to be fulfilled in connection with a capillary-type electrophoresis process, since no jumps in the field strength curve will occur during the subsequent application of the high voltages to the two ends of the capillary filled with a buffer liquid.

It follows that the method according to the present invention is suitable for controlling the field strength and, in particular, for concentrating the decreasing field strength in predetermined sections of the capillary.

Figure 3:
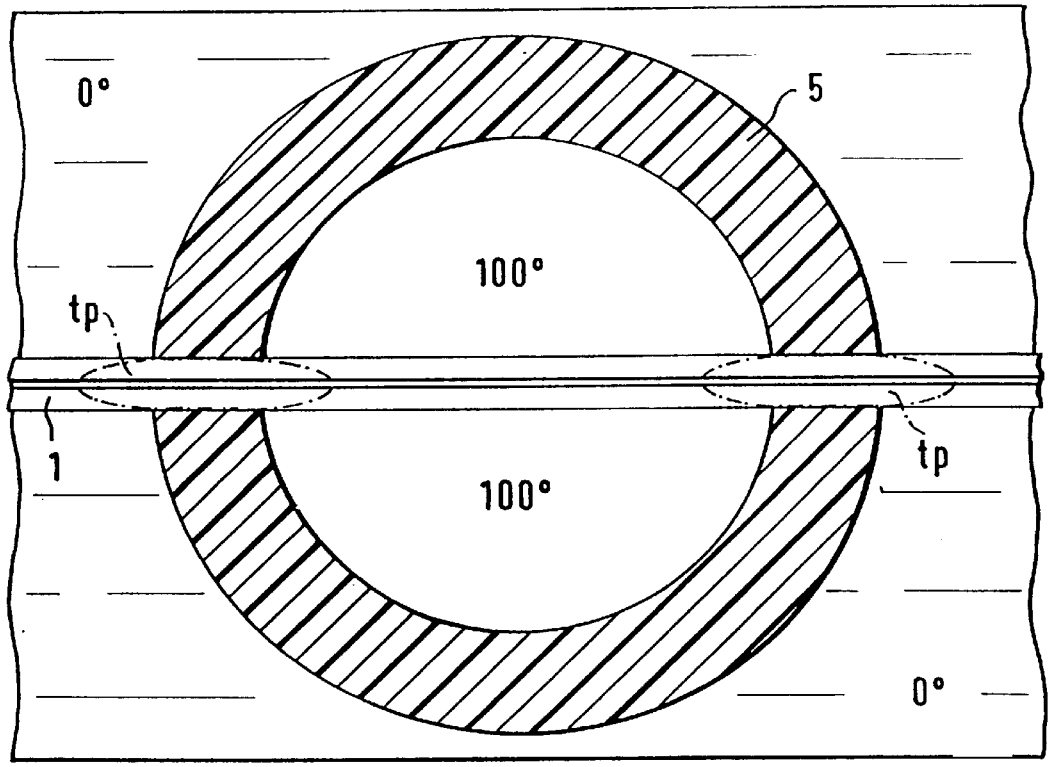
FIG. 3 shows a sectional view through a hose and a capillary.
Figure 4:
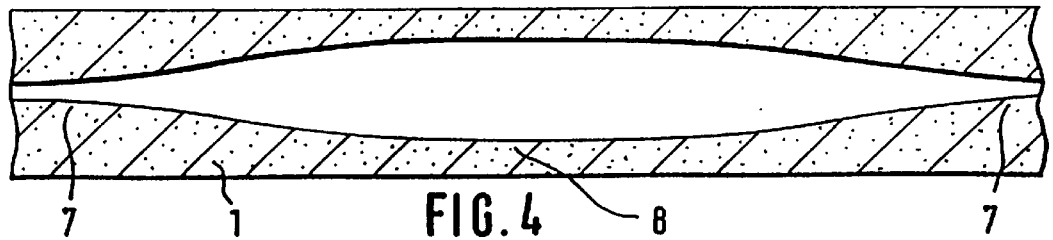
FIG. 4 shows a sectional view through a section of an additional embodiment of the capillary according to the present invention.

FIG. 3 shows a modified arrangement of the capillary 1 relative to the hose 5 upon carrying out the production method. In the arrangement shown in this figure, the capillary 1 extends through the hose 5 at right angles to the longitudinal axis of said hose. As can clearly be seen from the respective temperature profiles tp, a temperature distribution of from 0° Celsius to 100° Celsius is obtained in each case along the capillary 1 from the outer wall of the hose 5 to the inner wall thereof. When the production method described is carried out, such a design of the impressed temperature profile will result in a shape of the interior profile of the capillary 1 of the type shown clearly in FIG. 4. In this figure, it can be seen that, within a comparatively short capillary section whose length corresponds approximately to the width of the hose 5, a bubble is formed, which is defined by a continuous transition from the first capillary area 7 having a small inner width to the second capillary area 8 having a large inner width and then back to an additional first capillary area 7 having a small diameter.

Figure 5:
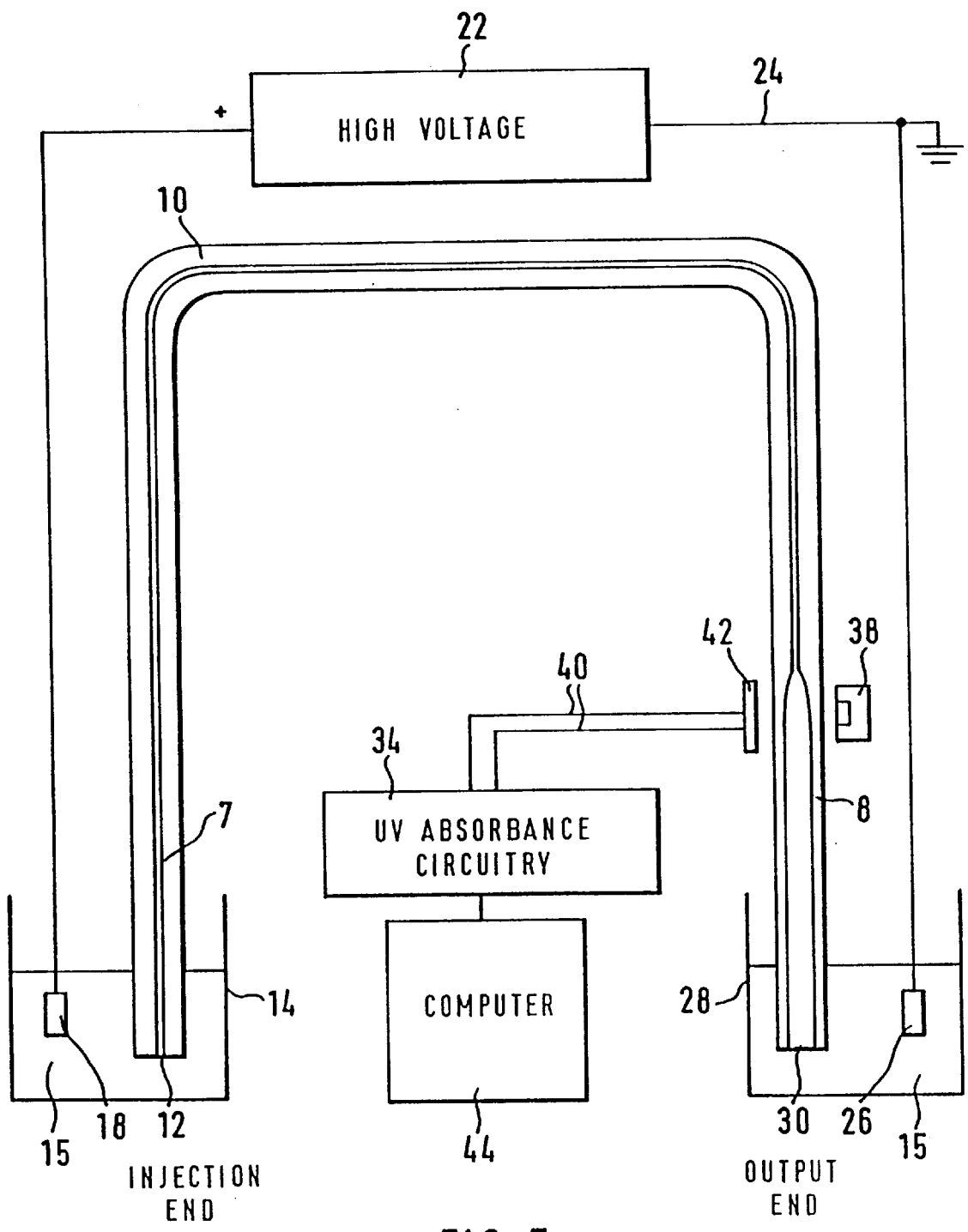
FIG. 5 shows a schematic representation of a capillary-type electrophoresis system.

FIG. 5 shows a capillary-type electrophoresis system, which is also referred to as Capillary Zone Electrophoresis System (CZE) and which includes a capillary 10 produced by means of the method according to the present invention. The capillary has an injection end 12 located in an injection reservoir 14. Said injection reservoir 14 supplies the capillary 10 with an electrolytic aqueous medium, which can also be referred to as buffer solution 15. A sample having unknown constituent parts is inserted into the injection end 12 by momentarily dipping said end 12 into a sample vial (not shown) and by drawing a small amount of sample into the capillary 10 by the application of voltage or pressure.

A high voltage power supply 22 is connected to a positive electrode 18 which is situated in the injection reservoir 14. A ground lead 24 connects the power supply 22 to a negative electrode 26, which is similarly located in an outlet reservoir. It should be understood that the polarities could be reversed, i.e. that the high voltage power supply 22 is connected to the positive electrode 18 and that the ground lead 24 connects the power supply 22 to the negative electrode 26. The outlet end 30 of the capillary 10 is placed in the outlet reservoir 28.

As can be seen on the right-hand side of FIG. 5, the second capillary area 8 having the enlarged inner width is located on the side of the outlet end 30 within the outlet reservoir 28, whereas the first capillary area 7 having the small inner width is located at the injection end 12. The second capillary area 8 of the capillary is positioned between a light source 38 and a detector 42, which receives light from said light source when said light has passed through the second capillary area 8, the right being there absorbed by the constituent parts of the solutes that are carried in the buffer solution 15. The detector 42 is connected to an ultraviolet absorbance evaluation circuitry 34 by leads 40. The measurements may be evaluated and displayed by a computer 44.

Figure 6:
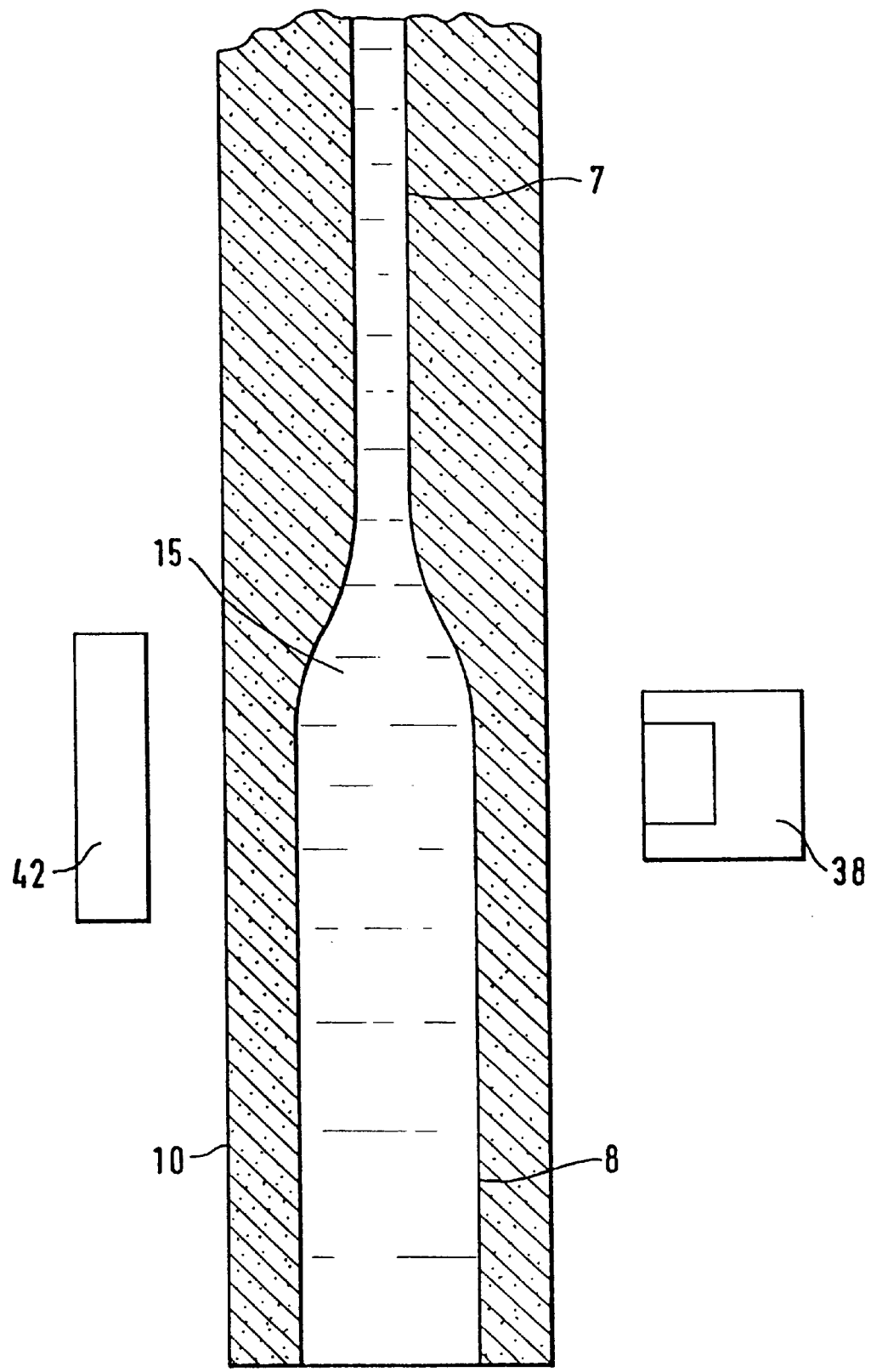
FIG. 6 shows a representation of a detail of the capillary provided in the device according to FIG. 5 for explaining the arrangement of said capillary relative to the detector device as well as its interior shape up to the outlet end.

The arrangement of the second capillary area 8 between the light source 38 and the detector 42 a short distance after the transition region from the first capillary area having the smaller inner width is shown in detail in FIG. 6. To the person skilled in the art it will be obvious that the voltage drop along the capillary takes place essentially along the first capillary area 7, whereas the voltage drop along the length of the second capillary area is practically negligible due to the enlarged inner width of said second capillary area.

It follows that an adequate arrangement of the capillary expansion in the transition region between the first and second capillary areas 7, 8 a short distance in front of the detector 42, when seen in the direction of flow, will have the effect that the field strength available will be concentrated in the capillary section in front of the detector 42, which is the important section with regard to the separation, loss voltage drops behind the detector 42, when seen in the direction of flow of the buffer solution 15, being practically impossible. A marked reduction of the time required for the analysis will thus be achieved.

In view of the fact that the capillary 10 according to the present invention has an essentially constant external structure throughout its length, and in view of the fact that possible outer layers, such as a polyamide layer, remain intact when said capillary is treated by means of the production method according to the present invention, a capillary which has been modified by the method according to the present invention can be used in a detector which was originally designed for standard capillaries having a constant inner width and a constant outer width.

Deviating from the preferred embodiment of the production method described at the beginning, it is also possible to expand a capillary 10, which has already been installed in the detector 42, at the location of detection, when a local rise in temperature is caused during the etching process; this can, for example, be done by applying hot gas by means of blowing or by means of microwave heating.

In this case, the time at which the etching process of the production method is finished can be determined by detection with the aid of the detection signal.

A comparatively slow transition from the smaller to the larger inner width over a distance of e.g. 1 to 2 mm permits a free choice of the most advantageous detection conditions by axially displacing the expanded capillary 10 in front of the detection window, which is determined by the light source 38 and the detector 42.

The optimum point for carrying out the detection depends on the necessary detection sensitivity; in any case, however, it is located close to the transition region.

It should be understood that the temperature-controlled etching process in accordeance with the invention can also be used for forming quartz detector cells for liquid chromatography detectors with specially adapted flow profiles

What is claimed is:

1. An electrophoresis device for detecting at least one constituent part of a sample, comprising:

a capillary including a first capillary area having a first inner width and a second capillary area having a second inner width which is enlarged in comparison with said first inner width, said first inner width merging with said second inner width continuously and smoothly and said first and second capillary areas having an unchanging outer width at least in their transition region, an input reservoir from which the first capillary area of the capillary extends, an outlet reservoir up to and into which the second capillary area of the capillary extends, a generator for producing an electric field between a buffer solution in the input reservoir and a buffer solution in the outlet reservoir; and an absorbance detector device comprising a light source and a light sensor arranged at the second capillary area of the capillary in close proximity to said transition region so as to detect the at least one constituent part of the sample.

2. A capillary according to claim 1 wherein the second capillary area having a second inner width, which is enlarged in comparison with said first inner width, extends from the transition region to said first capillary area up to the end of the capillary located on the outlet side.

3. An electrophoresis device for detecting at least one constituent part of a sample according to claim 2 wherein the detector device is an absorbance detector device.

4. An electrophoresis device for detecting at least one constituent part of a sample according to claim 2 wherein the detector device is a fluorescence detector device.

5. An electrophoresis device for detecting at least one constituent part of a sample, comprising:

a capillary having a first inner width and a second inner width which is enlarged in comparison with said first inner width, said first inner width merging with said second inner width continuously and smoothly in a transition region, and said capillary having an unchanging outer width at least in said transition region, a generator coupled to said capillary for producing an electric field across said first inner width and said second inner width of said capillary; and a detector, arranged proximate to said second inner width and in close proximity to said transition region so as to detect said at least one constituent part of the sample.

6. An electrophoresis device according to claim 5, wherein said detector device is an absorbance detector device.

7. An electrophoresis device according to claim 5, wherein said detector device is a fluorescence detector device.

8. An electrophoresis device according to claim 5, wherein said capillary further comprises an injector end and an output end, wherein said injector end communicates with said first inner width and said output end communicates with said second inner width.

9. An electrophoresis device according to claim 8, wherein said generator comprises a first electrode coupled to said injector end and a second electrode coupled to said output end.

10. An electrophoresis device according to claim 8, further comprising:

an input reservoir from which said injector end extends, wherein said input reservoir supplies said capillary with an electrolytic aqueous medium; and an outlet reservoir up to and into which said output end extends.

* * * * *